United States Patent
Hengelein et al.

(10) Patent No.: US 10,426,419 B2
(45) Date of Patent: Oct. 1, 2019

(54) METHOD AND MAGNETIC RESONANCE APPARATUS FOR SETTING ACQUISITION PARAMETERS OF A SCAN PROTOCOL

(71) Applicant: Siemens Healthcare GmbH, Erlangen (DE)

(72) Inventors: Bernd Hengelein, Neunkirchen a. Br. (DE); Kirstin Jattke, Nuremberg (DE); Christof Krellmann, Erlangen (DE); Wolfgang Trumler, Spardorf (DE)

(73) Assignee: Siemens Healthcare GmbH, Erlangen (DE)

( * ) Notice: Subject to any disclaimer, the term of this patent is extended or adjusted under 35 U.S.C. 154(b) by 154 days.

(21) Appl. No.: 15/710,330

(22) Filed: Sep. 20, 2017

(65) Prior Publication Data

US 2018/0078227 A1 Mar. 22, 2018

(30) Foreign Application Priority Data

Sep. 21, 2016 (DE) .......................... 10 2016 218 110

(51) Int. Cl.
| | |
|---|---|
| A61B 6/00 | (2006.01) |
| A61B 5/055 | (2006.01) |
| A61B 5/00 | (2006.01) |
| A61B 6/03 | (2006.01) |
| G01R 33/48 | (2006.01) |
| G01R 33/54 | (2006.01) |
| G01R 33/483 | (2006.01) |
| G01R 33/56 | (2006.01) |

(52) U.S. Cl.
CPC .............. *A61B 6/488* (2013.01); *A61B 5/055* (2013.01); *A61B 5/7271* (2013.01); *A61B 6/03* (2013.01); *G01R 33/48* (2013.01); *G01R 33/546* (2013.01); *G01R 33/4835* (2013.01); *G01R 33/5608* (2013.01); *G06T 2207/30004* (2013.01)

(58) Field of Classification Search
CPC .. G01R 33/48; G01R 33/546; G01R 33/4835; G01R 33/5608; G06T 2207/30004; A61B 6/488; A61B 6/03; A61B 5/055; A61B 5/7271
See application file for complete search history.

(56) References Cited

U.S. PATENT DOCUMENTS

| | | | | |
|---|---|---|---|---|
| 6,134,464 A | * | 10/2000 | Tan ..................... | G01R 33/4833 324/309 |
| 2003/0139660 A1 | * | 7/2003 | Tatebayashi ........... | A61B 5/055 600/407 |
| 2015/0091569 A1 | * | 4/2015 | Shinoda ................. | A61B 5/055 324/309 |

* cited by examiner

*Primary Examiner* — Rodney A Bonnette
(74) *Attorney, Agent, or Firm* — Schiff Hardin LLP

(57) ABSTRACT

In a method and magnetic resonance (MR) apparatus for setting acquisition parameters of a scan protocol, in an operator control console, for a planned MR acquisition procedure of slice groups rotated with respect to one another through an angle relative to an axis of rotation, each containing at least one slice, a graphical representation of the slice groups is used for operator specification of the angle and/or the number of slice groups. After a graphical selection of a starting slice group by a user and selection of a radial slice group operating mode when a first operator action of the user is performed via an input device, the slice group number is increased while the angle is reduced. When a second operator action is performed via the input device, the slice group number is reduced while the angle is increased. The graphical representation is simultaneously updated in each case.

17 Claims, 3 Drawing Sheets

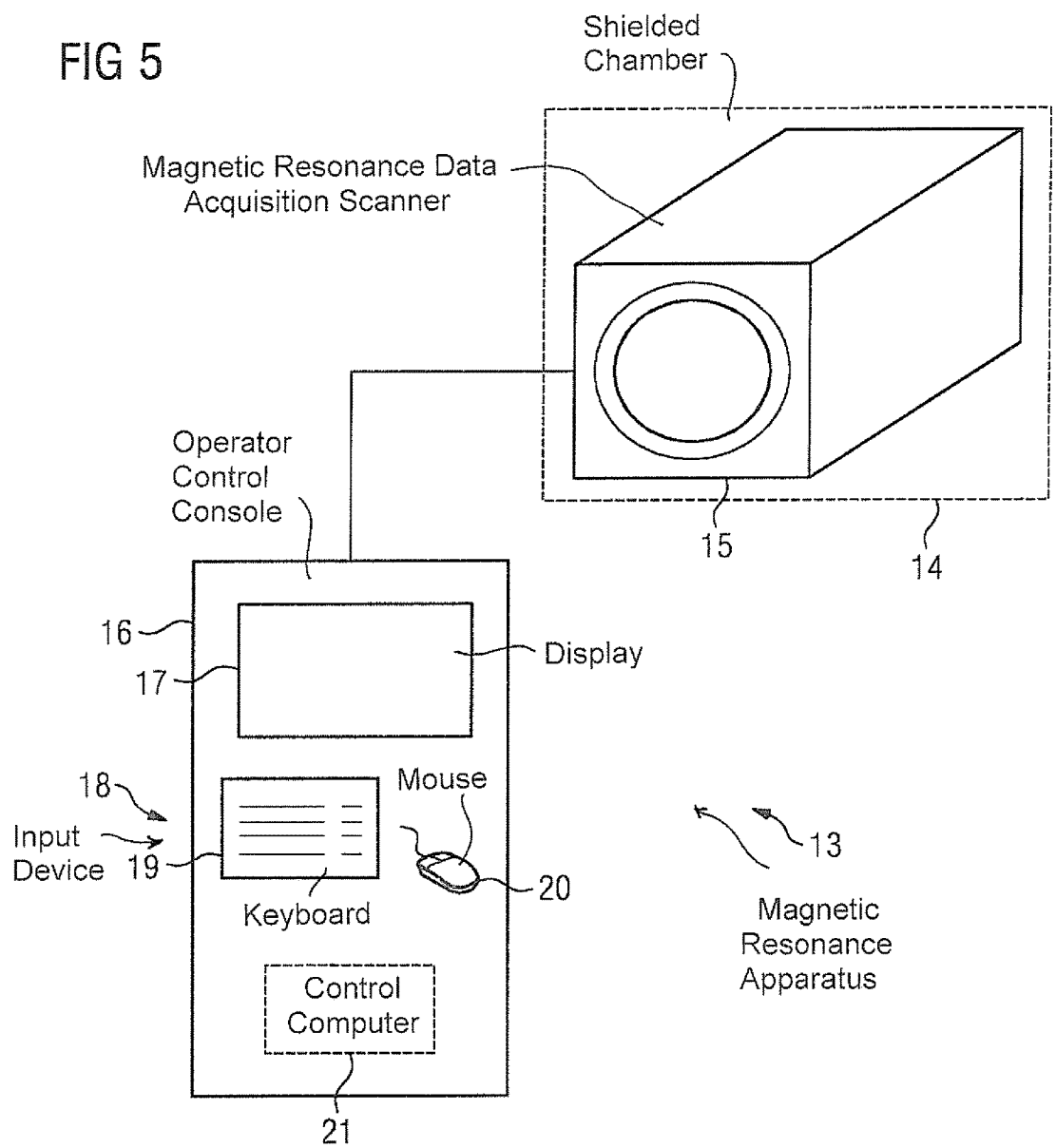

METHOD AND MAGNETIC RESONANCE APPARATUS FOR SETTING ACQUISITION PARAMETERS OF A SCAN PROTOCOL

BACKGROUND OF THE INVENTION

Field of the Invention

The present invention concerns a method for setting acquisition parameters at an operator control console, of a scan protocol for a planned acquisition procedure to be executed by a magnetic resonance apparatus, wherein the acquisition procedure includes an acquisition of slice groups rotated with respect to one another through an angle relative to an axis of rotation, each slice group containing at least one slice. The invention also concerns a magnetic resonance apparatus and an electronically readable data medium for implementing such a method.

Description of the Prior Art

Magnetic resonance apparatuses or systems are well known, magnetic resonance imaging having become a virtually indispensable imaging modality, particularly in medical applications. In such scenarios, magnetic resonance data are often acquired in slices or slice groups, which are defined in the form of acquisition parameters as part of a scan protocol with which the magnetic resonance apparatus is controlled in the course of an acquisition procedure. The acquisition parameters are in this case entered during the planning of the magnetic resonance measurement, i.e. the acquisition procedure, via an operator control console, namely via a computer thereof. Specifically with regard to the positioning of the slices relative to the anatomy of a patient, proposals have been made that also permit graphical planning. For example, it is possible to select a slice manipulation operating mode at the operator control console, in which slice manipulation operating mode at least one slice of a slice group, which is to be acquired in an acquisition procedure, is represented as a graphical object that can be manipulated on a screen by an operator. It is known for this purpose, for example, to provide a translation function that allows the translational displacement of the slice group, a resizing function for adjusting the size of the slices of the slice group, and a rotation function for rotating the slices of the slice group. The operator is given a visual feedback, since the operator receives the slices of the slice group displayed as an overlay to the anatomy that is to be scanned, and accordingly can manipulate them such that the acquisition region desired by him/her is covered in the form desired by him/her.

It should be noted that, as used herein, a slice can contain just a single slice.

Beyond the simple positioning of a slice group having at least one slice, there are many other acquisition parameters that have to be defined for a scan protocol, only some of which can be derived from the completed positioning of a slice group. For such acquisition parameters, it is known to define these by the entry of actual acquisition parameter values in a corresponding input mask.

A more recent, and now more frequently employed, acquisition technique is the so-called "radial slices" method. In this case the slices are not present in the form of a slice stack, but are rotated with respect to one another through a uniform angle around a fixed axis of rotation. Here, an axis of rotation extending through the center point of all of the slices generally serves as the axis of rotation, which runs along a common extension direction of the slices, in particular along the length or width. In the case of two slices or slice groups, the second slice group is rotated through 90° relative to the starting slice group, and in the case of three slice groups, angles of 60° lie between each of the slices, etc. In order to be able to enter the acquisition parameters of such "radial slices", the operator must enter acquisition parameters as values in a special input mask. For example, the operator must enter the angle or the number of slice groups, since in this technique a mathematical relationship exists between the acquisition parameters angle and slice group number. A visual check of the planning carried out in this way is at present possible for the operator at the earliest following the confirmation of the input and the determination of the corresponding scan protocol in a separate, non-interactive representation. Consequently, the graphical planning working practice is interrupted at this point, which is undesired and represents a non-intuitive procedure.

SUMMARY OF THE INVENTION

An object of the invention is to provide a planning acquisition procedure wherein slice groups are rotated with respect to one another, which is easy to implement, and that integrates seamlessly into existing graphical planning systems, and is intuitive for the operator.

This it is achieved according to the invention by a method of the type cited in the introduction but wherein, in order to support the specification of the angle and/or the number of slice groups on the operator console screen, a graphical representation of the slice groups is used. After a graphical selection of a starting slice group by a user and selection of a radial slice group operating mode, when a first operator action of the user is then performed via an input device, the slice group number is increased while the angle is reduced. When a second operator action is performed via the input device, the slice group number is reduced while the angle is increased. The graphical representation is simultaneously updated in each case.

In order to simplify the entry of acquisition parameters for defining slice groups rotated with respect to one another that are to be acquired, i.e. in order to define a so-called "radial slice group", for an operator, in particular to permit a continuation of a graphical planning process also for the purpose of defining the slice group number and the angle, a special two-step planning procedure is used according to the invention. In a first step, the user selects, preferably also with graphical support, a starting slice group, which in addition to at least one first slice group of the "radial slice group" (RSG), also determines the axis of rotation, the slice position and the slice extent (slice size). Thereafter, a radial slice group operating mode is selectively activated in which a first operator action and a second operator action, which preferably are designed to have opposite effects, are available for the second step. In the second step, the operator interacts in the radial slice group operating mode with the graphical object representing the slice groups, i.e., an actual interaction with the graphical object assigned to the starting slice group, using the first and the second operator actions, in order to select the desired slice group number or the desired angle (which are mathematically related). The invention thus achieves a particularly advantageous extension, proceeding from existing graphical planning possibilities, with regard to slice groups rotated with respect to one another.

This achieves the advantage that the operator, when inputting acquisition parameters, does not need to interrupt his/her customary graphical interaction, and a completely different approach to the positioning or definition of the slices does not have to be employed. Furthermore, the operator has no need to enter any information as actual parameter values, since the actual parameter values can easily be derived from the operation and the system status. The latter applies also to the aforementioned axis of rotation, which is beneficially already definable by the selection of the starting slice group, and the like. The invention also accommodates the operator in the sense that the definition of the acquisition parameters corresponds to natural hand-eye coordination. The operator sees the object that the operator wishes to manipulate/rotate, such that an intuitive interaction with the operator control console ensues. The operator is immediately able to recognize the consequences of the first operator action or the second operator action, and therefore visually decide during the interaction whether the chosen number or chosen angle meets the desired requirements.

In this context it is also particularly beneficial for the graphical representation to be realized in a location-true manner as an overlay on an image of the anatomy of the patient to be scanned in the acquisition procedure, this image having been derived from previously acquired magnetic resonance data of the patient to be scanned in the acquisition procedure. As is known from other graphical slice planning approaches, the graphical objects representing the slice groups can be represented as an overlay on an image of the anatomy of the patient that has preferably been derived or reconstructed from previously acquired magnetic resonance data of the patient. For example, such previously acquired magnetic resonance data can be from a survey scan known as a localizer. Considering that different views of the anatomy can usually be derived from magnetic resonance data of this type or from other anatomical data, a beneficial embodiment also provides in this context for the image to be selected at the operator console, for example as a slice that is to be represented. This is beneficial, since normally slice orientations of slice groups contained as graphical objects in the representation are specified at least partially in relation to the image plane or representation plane, for example as an extension disposed perpendicularly to the image plane. When there is a change of image, other slice groups can accordingly be defined and/or the representation can be adjusted to the orientation of the new image. Overall, the intuitive manner of operation can be enhanced further in the method according to the invention through the relation to the anatomy of the patient achieved by overlaying.

It can furthermore be beneficial, at least in the radial slice group operating mode, for the representation to be determined with only one representative slice, in particular the central slice, of each slice group. This means that, in the interest of a more intelligible and clearer representation, particularly with regard to the rotation of the individual slices relative to one another, it is sufficient, at least in the radial slice group operating mode, to represent a single slice of the slice group, preferably the central slice. It should also be noted that in most cases, when such "radial slices" are used, only one slice is acquired in each orientation anyway, i.e. the slice groups in most cases contain only one slice anyway. It should be pointed out here that it is beneficial, when a number of slice groups were provided in the starting slice group for graphical selection of a starting slice group, to mask out all slices except the representative slice for the radial slice group operating mode. It may also be provided to specify generally for the radial slice group operating mode that a slice group may contain only one slice, such that as a consequence only one slice is then acquired for each angle, as represented for the operator in the radial slice group operating mode.

In a preferred embodiment of the invention, the graphical selection of the starting slice group is made in a slice manipulation operating mode in which the first and the second operator actions serve for rotating a represented slice group, such that when the radial slice group operating mode is selected, the rotation function is replaced by a setting function for the number and/or the angle. Starting from the slice manipulation operating mode, the rotation function is therefore blocked and replaced so that the operator can continue to use the operator actions known to him/her from the rotation function for a purpose likewise related to a rotation, namely for the definition of slice groups rotated with respect to the starting slice group. An intuitive transition that is easy for an operator to learn is created in this manner and is furthermore easy to realize, since technically there is no need to provide any new operator actions.

In this context it is preferred for at least one of a translation function and a resizing function is also realized in the slice manipulation operating mode for the purpose of translating a represented slice group and for adjusting the size of a represented slice group in the presence of at least one further operator action assigned thereto in each case. The translation function and/or resizing function can also be kept active in the radial slice group operating mode. The operator thus can proceed from a slice planning interface that is generally known to him/her, in which the operator can move slices or slice groups by means of the translation function, increase and/or decrease their size by the resizing function, and rotate the slice group, particularly in the image plane or representation plane, by the rotation function. As is generally known to him/her, the operator can choose a position, orientation and size of the starting slice group, which can also specify the slice positions and the axis of rotation as well as the size of the slices of the slice groups, which will be explained in more detail below. The operator then selects the radial slice group operating mode, in which the rotation function is accordingly replaced by the setting function, though beneficially the translation function and the resizing function are kept active so that the operator can also still adjust these subsequently via the functions known to him/her, if the operator realizes that either the position or size of the slice group is not quite suitable.

As noted, in a preferred embodiment of the invention the slice position of the starting slice group and/or the axis of rotation for the rotation, particularly within the scope of the selection of the starting slice group and/or of the translation function, are determined by positioning the starting slice group, in particular as the center point of a representative slice of the starting slice group or extending through the center point. In this case the axis of rotation is defined as a basic setting extending through the center point perpendicularly to the image or representation plane, so that the display of the slice groups is also possible in an ideal manner during the setting of the number and/or angle without the need for recourse to perspective views and the like. Preferably, the axis of rotation can be displayed in the graphical representation, for example as the center point of the representative slice, which may, if necessary, also be provided in an upstream slice manipulation operating mode. In other words, the operator already specifies the slice position, the slice size and the axis of rotation in an intuitive manner in the first step by selection of the starting slice group, before the slice group number and/or the angle can then be set in the second step using the first operator action and the second operator action.

It should also be noted that, in addition or alternatively to a slice manipulation operating mode, a selection operating mode may be provided in which a number of slice groups, for example frequently used slice groups, are proposed for use and the operator can choose one of these slice groups as the starting slice group or, as the slice group that is still to be manipulated prior to the selection from the starting slice group.

It may furthermore be advanced intuitive operation if the starting slice group is represented as distinguishable from further slice groups added by means of the first and/or the second operator action. The operator recognizes in a simple manner from which slice group the operator started in his/her selection of a slice group number or angle, since the operator can easily recognize added slice groups.

In another embodiment of the present invention, the first and the second operator actions are a common, sustaining operator control action, wherein upon cessation of the common operator control action, the set angle and/or the set slice group number are/is stored and the radial slice group operating mode is terminated. Such a common, sustained operator control action can be the pressing of a button of a computer mouse or the like. Thus, while the common operator control action is sustained, the first or the second operator action can be completed by a further operator control action. In the example of the computer mouse, this can be a shifting of the mouse and/or a turning of a scroll wheel of the computer mouse, so that slice groups are accordingly added or removed. With the termination of the sustaining common operator control action, the operator now also terminates the radial slice group operating mode, such that the last configuration shown in the graphical representation and its associated acquisition parameters, i.e. the angle and/or the slice group number, are carried over accordingly. With the termination of the radial slice group operating mode, either the graphical planning can be terminated completely, or the planning procedure may switch back into a slice manipulation operating mode, for example. In this embodiment, the choice of the slice group number and/or the angle is therefore made in a quick, uncomplicated and yet intuitive manner with little interaction.

It is also beneficial for after termination of the radial slice group operating mode, at least one further acquisition parameter of the scan protocol to be derived from the set angle and/or the set slice group number and/or the set axis of rotation and/or the set slice position and/or the set slice size of the starting slice group. It is beneficial to perform an immediate update of the scan protocol, which may also contain acquisition parameters derived from the acquisition parameters that are settable here, only outside of the radial slice group operating mode so that excessive computational overhead can be avoided and a fluid, easily readable graphical representation is also possible when the first and the second operator actions are performed.

Preferably, the input device is a computer mouse, and the first and the second operator actions are a movement of the computer mouse and/or of a scroll wheel of the computer mouse in different directions and/or the pressing of a button of the computer mouse as a common, sustaining operator control action. Thus, for example, a common operator control action may be to press the left mouse button of the computer mouse and keep it pressed, whereupon either the first or the second operator action is now completed by moving the computer mouse or moving a scroll wheel of the computer mouse in opposite directions. This is a variant of the operator actions that is simple to implement and easy to use for an operator. The operator actions thus include the common, sustained component, by which it is also possible to check for a termination that is to be performed in order to end the radial slice group operating mode.

It is furthermore preferred for possible settable slice group numbers and/or angles to be predefined or predefinable, so only limited settable slice group numbers and/or angles are selected when the first or the second operator action is used. Generally, when slices rotated with respect to one another are used, only certain values are used in any case for the slice group number or the angle. For example, the number of slice groups can be limited to values of 3, 6, 12, 18, 24, 30 and 36. This enables the operator to be relieved of the task of considering values for the acquisition parameters that in most cases would be ruled out anyway. In this context it is beneficial for the possible settable slice group numbers and/or angles to be configured by an operator via the operator control console and/or to be retrieved from a user profile of the operator. In this way, preferences of the operator or restrictions resulting from the operator's diagnostic field can also be taken into account so that, for example, certain permitted values for the number and/or the angle can be entered, or predefined slice group numbers and/or angles can be selectively ruled out. In this way, the operator can arrive more quickly at his/her desired acquisition parameters. Predefined operator-side parameter values can be stored in a user profile of the operator, for example.

It should also be noted that, following a final confirmation by the operator, the scan protocol can then be used for the acquisition of magnetic resonance data by operation of the scanner of the magnetic resonance apparatus, as is generally known in the art. For example, the scan protocol can be displayed again with the further acquisition parameters derived in part also from acquisition parameters entered by the method according to the invention, and the like.

The invention also concerns a magnetic resonance apparatus, having an operator control console having a control computer configured to perform the method according to the invention. All statements made with respect to the method according to the invention apply to the magnetic resonance apparatus according to the invention, so the cited advantages can likewise be obtained.

The present invention also encompasses a non-transitory, computer-readable data storage medium encoded with programming instructions (program code) that, when the storage medium is loaded into a computer or computer system of a magnetic resonance apparatus, cause the computer or computer system to operate the magnetic resonance apparatus in order to implement any or all of the embodiments of the method according to the invention, as described above.

BRIEF DESCRIPTION OF THE DRAWINGS

FIG. 5 shows a magnetic resonance system according to the invention.

DESCRIPTION OF THE PREFERRED EMBODIMENTS

An exemplary embodiment of the method according to the invention is explained in more detail below with reference to the schematic diagrams of FIGS. 1 to 4. This concerns a graphical slice planning method that has been extended to include the definition of acquisition parameters when using slices rotated with respect to one another, or slice groups generally containing at least one slice. It should be noted that the graphical representations shown here are basically presented as overlays on (selectable) images of the anatomy of the patient that is to be scanned, in order to be able to permit a corresponding intuitive orientation on the part of the operator. For clarity of illustration, further details of these images are not shown, and it should furthermore be noted that the images may be derived from previously acquired magnetic resonance data of the patient, in particular from magnetic resonance data of a localizer scan.

Figure 1:
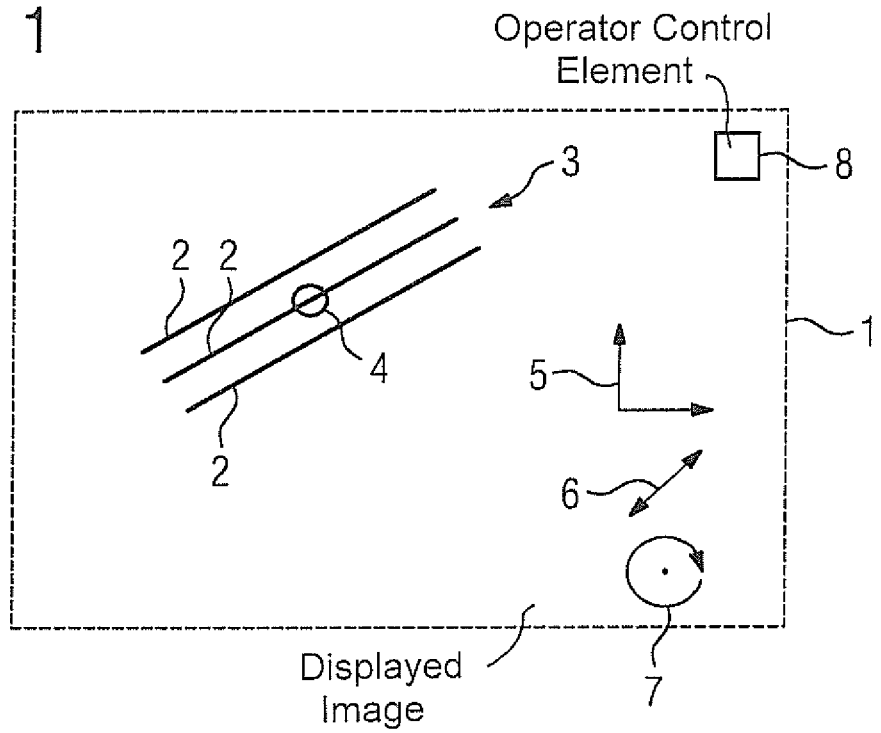
FIG. 1 shows a graphical representation in a slice manipulation operating mode.
Figure 2:
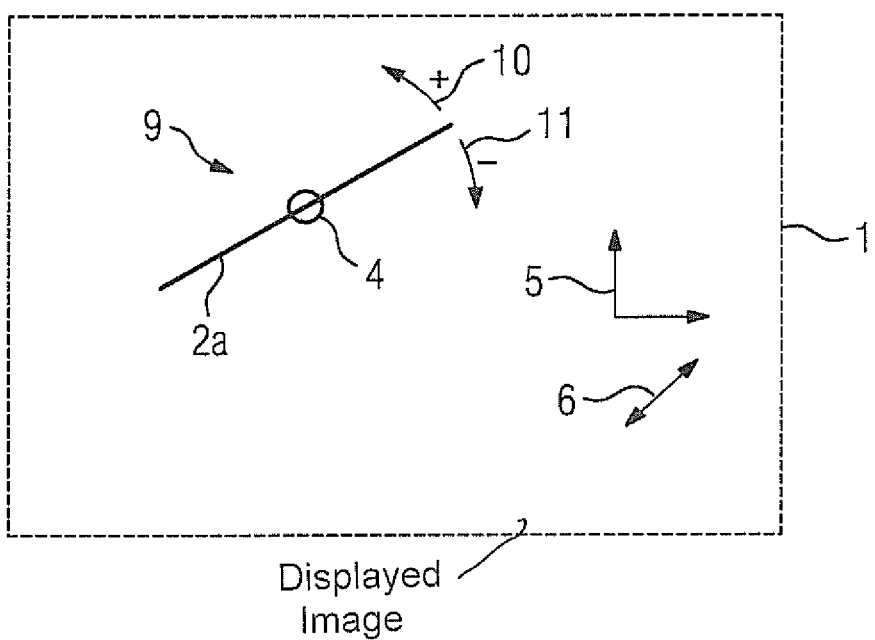
FIG. 2 shows an initial graphical representation in a radial slice group operating mode.

FIG. 1 shows a graphical representation in a slice manipulation operating mode, from which the exemplary embodiment of the method according to the invention described here proceeds. As can be seen, slices 2 of a slice group 3 are shown overlying the image 1, which is represented here only schematically. Also shown is the center point 4 of the representative, central slice of the slice group 3, which, in the present case, still has three slices 2 as an example. In order to be able to adjust the position and embodiment of the slice group 3 to his/her needs, the operator is provided with several manipulation functions, specifically a translation function indicated by the arrows 5, a resizing function, described by the arrows 6, for the slices 2, and a rotation function, described by the arrow 7, for the slice stack 3, which rotation function plays a special role for the further steps of the method described here.

The slice manipulation mode according to FIG. 1 is used by the operator in the present case to place a starting slice group in relation to the slice position of the representative slice (center point 4) and with respect to the subsequent location of the axis of rotation, as well as to specify the slice size at least provisionally. The translation function and the resizing function and, if necessary, the rotation function, are used for this purpose.

It should be noted that other types of placement of the starting slice group may also be used in other exemplary embodiments, for example the setting of an axis of rotation by a first mouse click and the dragging of the width by a second mouse click, though this is less preferred.

Once the operator is satisfied with the placement, the operator activates a radial slice group operating mode (which is explained in more detail with reference to FIG. 2), for example by a schematically indicated operator control element 8 or a specific operator action on the part of the operator control device, on the display device of which the graphical representation is shown. The slice group 3 of FIG. 1 now forms the starting slice group 9, the number of slices 2 in the slice group 3 having been reduced automatically to a single slice 2a, namely the representative, central slice 2, since in the present example only acquisition processes with slice groups rotated with respect to one another and containing precisely one slice 2, 2a are to be considered. The graphical representation furthermore continues to include the center point 4, since the latter also serves for defining the axis of rotation, which in the present example is chosen as extending through the center point 4 perpendicularly to the image plane or representation plane. The size of the slices that are to be acquired subsequently can be deduced from the representation size of the slice 2a.

Whereas the translation function (cf. arrow 5) and the resizing function (cf. arrow 6) are retained for the operator in order to enable the latter to make corrections subsequently if necessary, the rotation function (arrow 7 in FIG. 1) has been replaced by a setting function for the slice group number and the angle between the slices of the slice groups. This setting function is symbolized in the present example by the arrows 10 and 11. Whereas conventionally there was a first operator action for the rotation function, which rotated the slice group 3 to the left, and a second operator action, which rotated the slice group 3 to the right, the first and the second operator actions in accordance with the invention now serve to increase the slice group number and decrease the slice group number, respectively, as indicated by "+" and "−" in FIG. 2.

The first and the second operator actions are performed via an input device of the operator control console, which in the present example is a computer mouse. As a common operator control action to be performed without interruption, the first operator action and the second operator action are, in the present example, the pressing of the left mouse button. A movement of the mouse in opposite directions completes the first or the second operator action.

Figure 3:
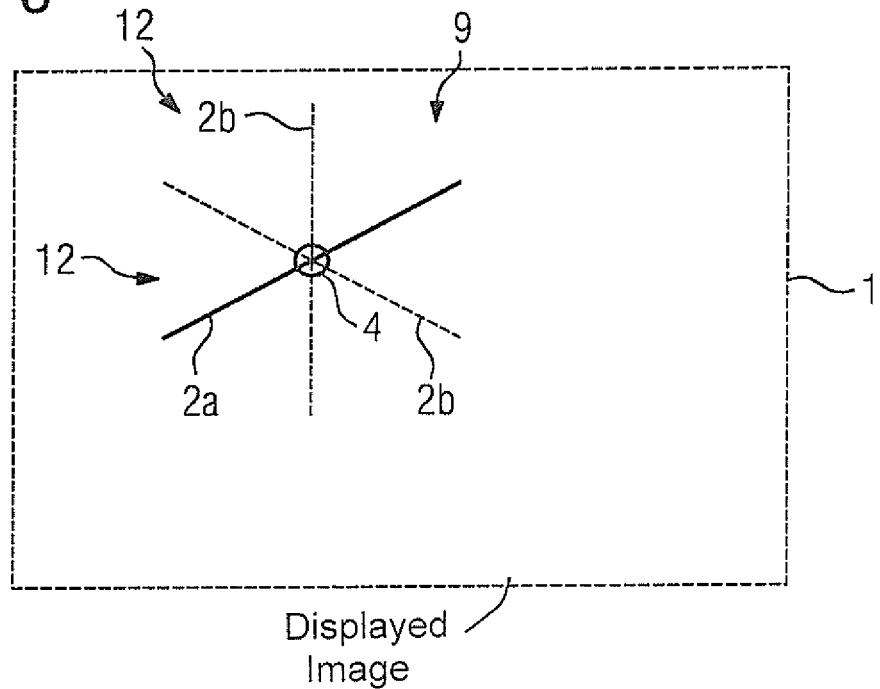
FIG. 3 shows a further graphical representation in the radial slice group operating mode after a first operator action has been performed.

FIG. 3 shows the graphical representation after the first operator action has been carried out. As be seen, in addition to the starting slice group 9, there are two further slice groups 12, each of which again contains a slice 2b represented by a dashed line. The slice group number therefore amounts to three, the angle to 60°. It should be noted that only certain slice group numbers may be set by means of the first and the second operator action, which can be used in a judicious manner, which means that the options for setting said acquisition parameter are limited. An operator-side restriction can be added for this purpose, for example when the operator does not require some of the basically and generally settable slice group numbers, such that the time needed for setting the slice group number as an acquisition parameter can be further reduced for the operator. Such an operator-side configuration can be stored in a user profile of the operator. Generally allowed values for the acquisition parameter "slice group number" are 3, 6, 12, 18, 24, 30 and 36 in the present example.

As can also be seen from FIG. 3, the graphical representation is repeatedly updated each time the operator action is performed, i.e. the slice groups 9, 12 are visualized so that the operator can intuitively register against the background of the image whether the current selection is suitable for him/her.

Figure 4:
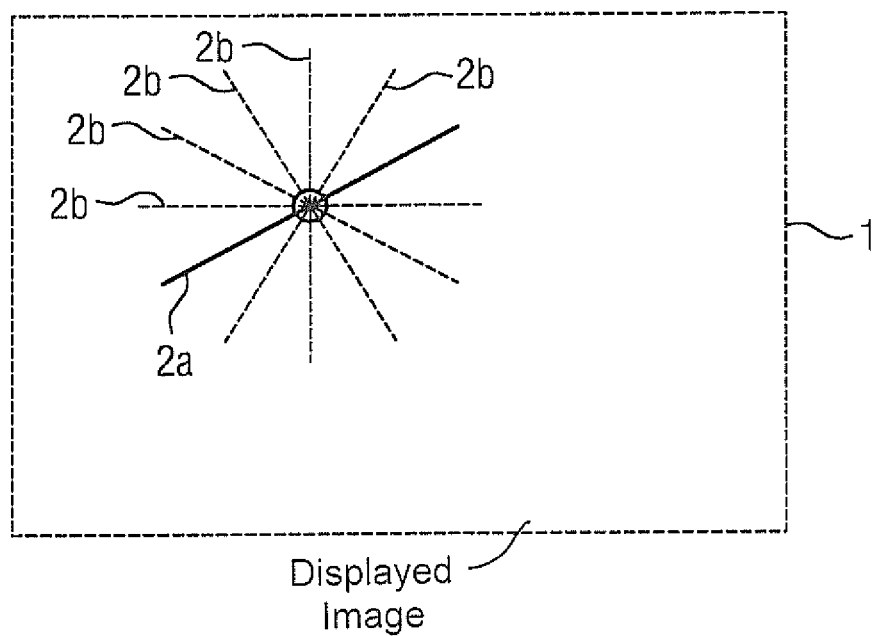
FIG. 4 shows a further graphical representation in a radial slice group operating mode after the first operator action has been performed.

FIG. 4 shows the graphical representation after the first operator action has been performed a further time, such that now six slice groups 9, 12, each containing one slice 2a, 2b, are shown. By performing the second operator action, the operator can go back again from FIG. 4 to FIG. 3, and from FIG. 3 to FIG. 2.

On account of the chosen processing mode, i.e. the radial slice group operating mode, and the interaction, the result is immediately visible, such that the current setting can be visually verified straightaway by the operator.

The exemplary embodiment described in the present case provides that upon termination of the common, sustained operator control action, in effect, therefore, the actuation of the left mouse button, the radial slice group operating mode is also terminated. Only now are the set acquisition parameters, in this case, therefore, the slice group number and the angle, imported into the scan protocol calculation, which means that only at this time are further acquisition parameters that are to be derived from the acquisition parameters "slice group number" and "angle" calculated and the scan protocol is updated accordingly. As soon as the scan protocol as a whole has been confirmed by the operator, the acquisition procedure can then be performed using the scan protocol.

FIG. 5 is a schematic illustration of a magnetic resonance apparatus 13 according to the invention. This apparatus 13 has a magnetic resonance data acquisition scanner 15 in a shielded chamber 14, as well as an operator control console 16 arranged outside of the shielded chamber 14. In the present example, the console 16 has a display 17 for graphical representations, as discussed with reference to FIGS. 1 to 4. The operator control console 16 additionally includes an input device 18, which in the present example includes a keyboard 19 and a computer mouse 20.

The operator control console 16 also has a control computer 21 configured to perform the method according to the invention.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for setting acquisition parameters of a scan protocol for a planned acquisition procedure to be conducted by a magnetic resonance (MR) apparatus, said method comprising:
   for an MR data acquisition procedure comprising acquisition of MR data from multiple slice groups, each slice group comprising at least one slice of an examination subject, presenting a graphical representation of said slice groups at a display screen of an operator control console of said MR apparatus;
   via a computer of said operator control console, allowing an operator to make entries into the computer that cause rotation of said slice groups with respect to each other through an angle relative to an axis of rotation, and to select a number of said slice groups;
   from said computer, displaying a starting slice group at said display screen, and receiving an entry into the computer that places said computer and said graphical representation in a radial slice group operating mode;
   in said radial slice group operating mode, controlling said graphical representation at said display screen from said computer in response to a first operator action in order to increase said slice group member while reducing said angle and, in response to second operator action that is different from said first operator action, to reduce said slice group number while increasing said angle; and
   from said computer, automatically and simultaneously updating said graphical representation with each of said first operator action said second operator action.

2. A method as claimed in claim 1 comprising:
   from said computer, also displaying an anatomical image of the examination subject on said display screen, and overlaying said graphical representation on said anatomical image with said slice groups in said graphical representation situated anatomically correctly on said anatomical image.

3. A method as claimed in claim 2 comprising configuring said graphical representation of said slice groups to display only one slice of a respective slice group.

4. A method as claimed in claim 3 wherein said only one slice is a central slice of the respective slice group.

5. A method as claimed in claim 1 comprising configuring said graphical representation of said slice groups to display only one slice of a respective slice group.

6. A method as claimed in claim 5 wherein said only one slice is a central slice of the respective slice group.

7. A method as claimed in claim 1 comprising, via an entry made by a user into said computer, placing said computer and said graphical representation in a slice manipulation operating mode, and selecting said starting slice group in said slice manipulation operating mode by selection entries made by a user via said computer, with said first and second actions in said slice manipulation operating mode causing rotation of the slice group represented in said graphical representation.

8. A method as claimed in claim 7 comprising, via said computer, also including one of a translation function and resizing function in said slice manipulation operating mode, said translating function causing translation of the represented slice group and said resizing function adjusting a size of the represented slice group, and executing said translation function or said resizing function in response to a further operator action via said computer, and also maintaining said at least one of said translation function and said resizing function so as to be active in said radial slice group operating mode.

9. A method as claimed in claim 8 comprising making said translation function active in said slice manipulation operating mode and, using said translation function, selecting at least one of a slice position of said starting slice and said access of rotation using said translation function.

10. A method as claimed in claim 1 comprising, from said computer, causing said starting slice group to be shown at said display screen with an appearance that is distinguishable from subsequent slice groups that are produced by either of said first or second operator actions.

11. A method as claimed in claim 1 comprising, in said computer, configuring said first and second operator actions as a common, sustained operator control action made via an input unit in communication with said computer, and wherein, upon cessation of said common operator control action, at least one of said angle, and said slice group number, is stored and the radial slice group operating mode is terminated.

12. A method as claimed in claim 1 comprising, after termination of said radial slice group operating mode, automatically deriving, in said computer, at least one further acquisition parameter of said scan protocol from at least one of said angle, said slice group number, said axis of rotation, and a slice position of the starting slice group.

13. A method as claimed in claim 1 comprising receiving said first and second actions into said computer via a computer mouse in communication with said computer, and wherein said first and second operator actions comprise at least one of a movement of said computer mouse, operation of a scroll wheel of said computer mouse in respectively different directions, and pressing a button of the computer mouse, as a common, sustained operator control action.

14. A method as claimed in claim 1 comprising, via said computer, providing limits as to at least one of an allowable number of slice groups and an allowable angle, and permitting, via said computer, said first and second operator actions to only be within said limit.

15. A method as claimed in claim 14 comprising allowing an operator to set or select, via said computer, said limit.

16. A magnetic resonance (MR) apparatus comprising:
   an MR data acquisition scanner operated by an operator control console, said operator control console comprising a computer in communication with a display screen;

for an MR data acquisition procedure comprising acquisition of MR data from multiple slice groups, each slice group comprising at least one slice of an examination subject, said computer being configured to present a graphical representation of said slice groups at said display screen of said operator control console;

said computer of said operator control console, being configured to allow an operator to make entries into the computer that cause rotation of said slice groups with respect to each other through an angle relative to an axis of rotation, and to select a number of said slice groups;

said computer being configured to display a starting slice group at said display screen, and to receive an entry into the computer that places said computer and said graphical representation in a radial slice group operating mode;

said computer being configured, in said radial slice group operating mode, to control said graphical representation at said display screen from said computer in response to a first operator action in order to increase said slice group member while reducing said angle and, in response to second operator action that is different from said first operator action, to reduce said slice group number while increasing said angle; and said computer being configured to automatically and simultaneously update said graphical representation with each of said first operator action said second operator action.

17. A non-transitory, computer-readable data storage medium encoded with programming instructions, said storage medium being loaded into a computer of an operator control console of magnetic resonance (MR) apparatus, said operator control console also comprising a display screen in communication with said computer, and said programming instructions causing said computer to:

for an MR data acquisition procedure comprising acquisition of MR data from multiple slice groups, each slice group comprising at least one slice of an examination subject, presenting a graphical representation of said slice groups at said display screen of said operator control console;

allow an operator to make entries into the computer that cause rotation of said slice groups with respect to each other through an angle relative to an axis of rotation, and to select a number of said slice groups;

display a starting slice group at said display screen, and receive an entry into the computer that places said computer and said graphical representation in a radial slice group operating mode;

in said radial slice group operating mode, control said graphical representation at said display screen from said computer in response to a first operator action in order to increase said slice group member while reducing said angle and, in response to second operator action that is different from said first operator action, to reduce said slice group number while increasing said angle; and automatically and simultaneously update said graphical representation with each of said first operator action said second operator action.

\* \* \* \* \*